US00PP12775P2

(12) United States Plant Patent
Glicenstein

(10) Patent No.: US PP12,775 P2
(45) Date of Patent: Jul. 16, 2002

(54) CHRYSANTHEMUM PLANT NAMED 'YOHAMILTON'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,662

(22) Filed: Mar. 15, 2000

(51) Int. Cl.[7] ..... A01H 5/00
(52) U.S. Cl. ..... Plt./289
(58) Field of Search ..... Plt./289

(56) References Cited

U.S. PATENT DOCUMENTS

PP6,125 P * 3/1988 Duffett ..... Plt./289

OTHER PUBLICATIONS

Copy of First page of EU 6433, dated Jul. 3, 2000.*
UPOV–ROM, 2001/3, Plant Variety Database, GTI Jouve Retrieval Software, citation for 'Yohamilton'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yohamilton', characterized by its upright and uniformly mounded plant habit; freely branching, dense and full plants; vigorous and strong plant growth; strong and dark green leaves; uniform flowering; excellent inflorescence form retention; early flowering, eight-week response time; large and full decorative-type inflorescences that are about 9.7 cm in diameter; bright yellow-colored ray florets; excellent winter performance; and excellent postproduction longevity with inflorescences and leaves maintaining good substance and color for about three to four weeks in an interior environment.

2 Drawing Sheets

BACKGROUND OF THE INVENTION

The present Invention relates to a new and distinct cultivar of Chrysanthemum plant, botanically known as *Dendranthema grandiflora* and hereinafter referred to by the cultivar name Yohamilton.

The new Chrysanthemum is a product of a planned breeding program conducted by the Inventor in Salinas, Calif. and Fort Myers, Fla. The objective of the breeding program is to create new potted Chrysanthemum cultivars with desirable inflorescence form and floret colors, good substance, and excellent postproduction longevity.

The new Chrysanthemum originated from a cross made by the Inventor in January, 1994, in Salinas, Calif., of a proprietary Chrysanthemum seedling selection identified as YB-6145 as the male, or pollen, parent with a proprietary Chrysanthemum seedling selection identified as YB-1421 as the female, or seed, parent. The new Chrysanthemum was discovered and selected by the Inventor as a single flowering plant within this population in May, 1995. The selection of this plant was based on its desirable inflorescence form and floret colors.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Yohamilton has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yohamilton'. These characteristics in combination distinguish 'Yohamilton' as a new and distinct Chrysanthemum:

1. Upright and uniformly mounded plant habit.
2. Freely branching, dense and full plants.
3. Vigorous and strong plant growth.
4. Strong and large dark green leaves.
5. Uniform flowering and excellent inflorescence form retention.
6. Early flowering, eight-week response time.
7. Large and full decorative-type inflorescences that are about 9.7 cm in diameter with numerous ray florets.
8. Bright yellow-colored ray florets.
9. Excellent winter performance.
10. Excellent postproduction longevity with inflorescences and leaves maintaining good substance and color for about three to four weeks in an interior environment.

Plants of the new Chrysanthemum are similar in ray floret coloration to plants of the cultivar, Iridon, disclosed in U.S. Plant Pat. No. 6,125. In side-by-side comparisons conducted in Fort Myers, Fla., plants of the new Chrysanthemum differ from plants of the cultivar Iridon in the following characteristics:

1. Plants of the new Chrysanthemum are more vigorous and taller than plants of the cultivar Iridon.
2. Plants of the new Chrysanthemum have larger leaves than plants of the cultivar Iridon.
3. Plants of the new Chrysanthemum have larger inflorescences than plants of the cultivar Iridon.
4. Plants of the new Chrysanthemum flower about one week earlier than plants of the cultivar Iridon.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top pf the first sheet comprises a top perspective view of a typical flowering plant of 'Yohamilton'.

The photograph at the bottom of the first sheet comprises a close-up view of a typical inflorescence and upper (left) and lower (right) surfaces of typical leaves of the cultivar Yohamilton.

The photograph on the second sheet comprises a close-up view of typical inflorescences of 'Yohamilton'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Salinas, Calif., under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Yohamilton.

Commercial classification: Decorative disbudded-type potted Chrysanthemum.

Parentage:

*Male, or pollen, parent.*—Proprietary Chrysanthemum seedling selection identified as YB-6145.

*Female, or seed, parent.*—Proprietary Chrysanthemum seedling selection identified as YB-1421.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative potted Chrysanthemum typically grown as a disbudded-type. Inverted triangle; stems mostly upright and somewhat outwardly spreading giving a uniformly mounded appearance to the plant. Vigorous and strong plant growth; excellent winter performance. Freely branching; about four lateral branches develop after removal of terminal apex (pinching); dense and full plants.

*Plant height.*—About 26 cm.

*Plant width.*—About 39 cm.

*Stem description.*—Diameter: About 3 mm. Texture: Pubescent. Color: Close to 146A.

*Foliage description.*—Arrangement: Alternate. Length: About 9.1 cm. Width: About 7.8 cm. Apex: Cuspidate. Base: Mostly truncate. Margin: Palmately lobed, sinuses between lateral lobes mostly divergent. Texture: Upper and lower surfaces with very fine pubescence; veins prominent on lower surface. Petiole length: About 2.6 cm. Petiole diameter: About 4 mm. Color: Young foliage upper surface: Darker than 147A. Young foliage lower surface: Darker than 147B. Mature foliage upper surface: Darker than 147A. Mature foliage lower surface: Darker than 147B. Venation upper surface: 147A to 147B. Venation lower surface: 147B.

Inflorescence description:

*Appearance.*—Decorative inflorescence form with elongated oblong-shaped ray florets with long corolla tube, spoon-like. Numerous ray florets, full inflorescences. Inflorescences borne on terminals above foliage. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences and leaves maintain good color and substance for about three to four weeks in an interior environment.

*Quantity of inflorescences.*—As a disbudded-type, all lateral inflorescences are removed to allow for maximum terminal inflorescence size. One inflorescence per lateral stem; about four inflorescences per plant.

*Inflorescence bud.*—Height: About 7 mm. Diameter: About 8 mm. Color: Close to 137A.

*Inflorescence size.*—Diameter: About 9.7 cm. Depth (height): About 2.5 cm. Diameter of disc: About 7 mm.

*Ray florets.*—Shape: Elongated-oblong, long corolla tube, spoon-like; concave. Orientation: Initially upright, then horizontal. Excellent inflorescence form retention. Length: About 4.4 cm. Width: About 9 mm. Apex: Emarginate. Margin: Entire. Texture: Smooth, glabrous, satiny. Number of ray florets per inflorescence: Very full, more than 300. Color: When opening: Green, 154A to yellow, 9A. Fully opened, upper surface: Bright yellow, 9A. Fully opened, lower surface: 9B to 9C.

*Disc florets.*—Shape: Tubular. Apex: Serrated. Length: About 5 mm. Width: Apex: About 1.5 mm. Base: About 1 mm. Number of disc florets per inflorescence: About 57. Color: Immature: 154A. Mature: Apex: Yellow, 9A. Mid-section and base: White, 155D.

*Reproductive organs.*—Androecium: Present on disc florets only. Anther color: 14A. Pollen amount: Scarce. Pollen color: 17A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yohamilton', as illustrated and described.

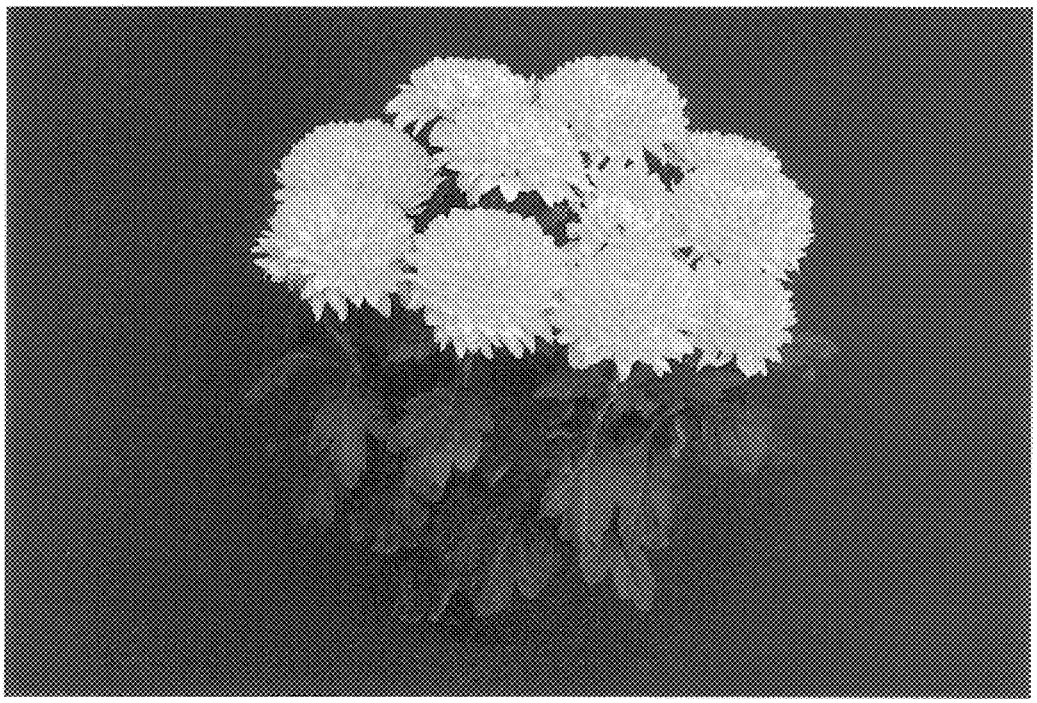
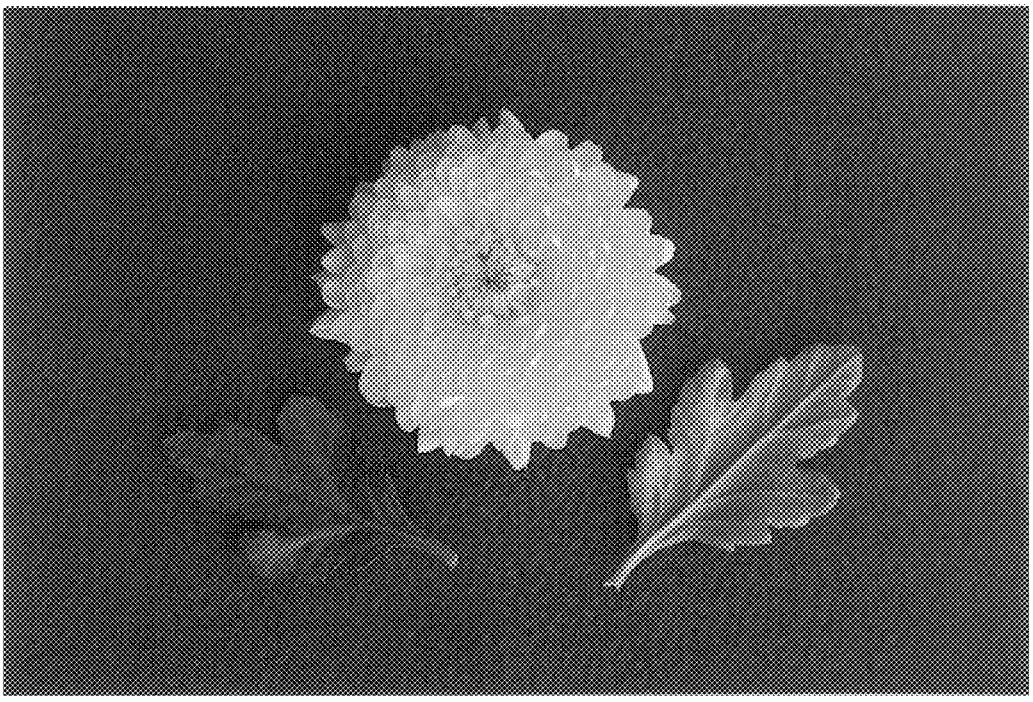

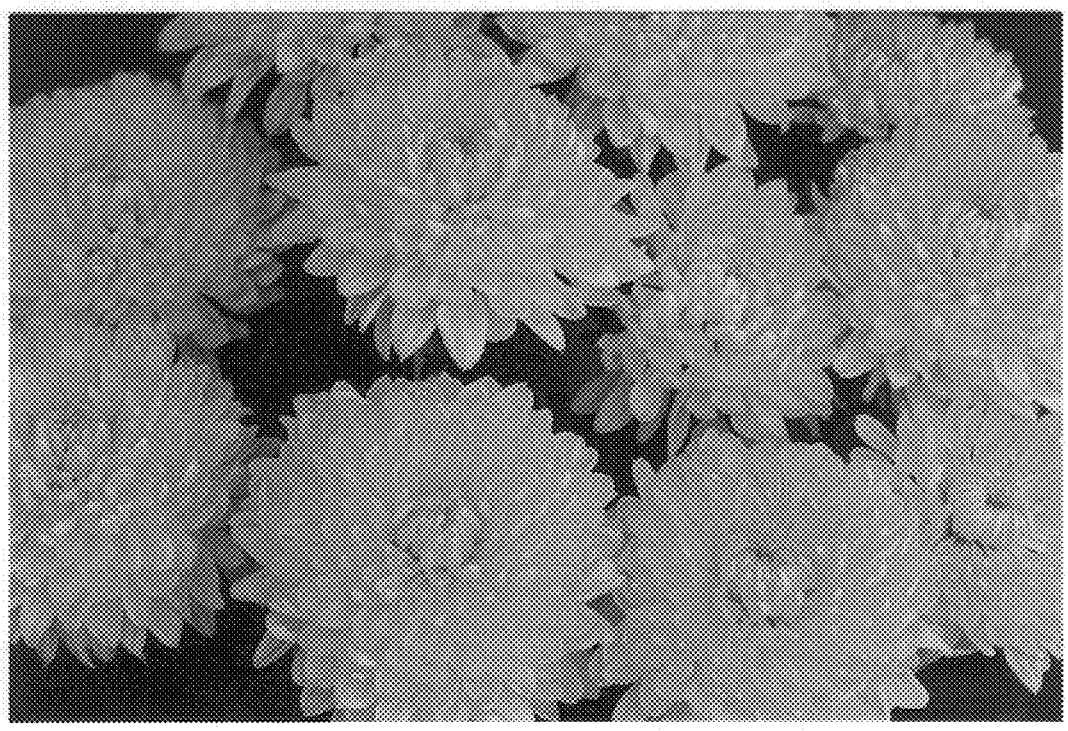

* * * * *